United States Patent
Kugler

(10) Patent No.: US 10,245,050 B2
(45) Date of Patent: Apr. 2, 2019

(54) METHODS FOR FACILITATING REVASCULARIZATION OF OCCLUSION

(71) Applicant: Teleflex Innovations S.à.r.l., Luxembourg (LU)

(72) Inventor: Chad Kugler, Buffalo, MN (US)

(73) Assignee: Teleflex Innovations S.à.r.l., Luxembourg (LU)

(*) Notice: Subject to any disclaimer, the term of this patent is extended or adjusted under 35 U.S.C. 154(b) by 407 days.

(21) Appl. No.: 15/340,026

(22) Filed: Nov. 1, 2016

(65) Prior Publication Data
US 2018/0092650 A1 Apr. 5, 2018

Related U.S. Application Data

(60) Provisional application No. 62/401,964, filed on Sep. 30, 2016.

(51) Int. Cl.
*A61B 17/22* (2006.01)

(52) U.S. Cl.
CPC .... *A61B 17/22* (2013.01); *A61B 2017/22001* (2013.01); *A61B 2017/22038* (2013.01);
(Continued)

(58) Field of Classification Search
CPC .......... A61B 17/22; A61B 2017/22041; A61B 2017/22067; A61B 2017/22001;
(Continued)

(56) References Cited

U.S. PATENT DOCUMENTS

| 4,762,130 A | 8/1988 | Fogarty et al. |
| 4,909,252 A | 3/1990 | Goldberger |

(Continued)

FOREIGN PATENT DOCUMENTS

| EP | 1815823 B1 | 12/2008 |
| EP | 1587447 B1 | 9/2012 |
| FR | 3018195 A1 | 9/2015 |
| JP | H09164191 A | 6/1997 |
| JP | 2002503986 A | 2/2002 |
| JP | 2005230579 A | 9/2005 |

(Continued)

OTHER PUBLICATIONS

Response to Final Rejection, filed Oct. 8, 2018, in U.S. Appl. No. 14/850,095.

(Continued)

*Primary Examiner* — Phong Son H Dang
(74) *Attorney, Agent, or Firm* — Gregory W. Smock

(57) ABSTRACT

This patent document discloses methods for facilitating revascularization of an occlusion in a blood vessel. A method can include engaging a first guide within a vessel wall adjacent to a distal cap of the occlusion and advancing the first guide, in a retrograde direction, to a subintimal position near a proximal cap of the occlusion. A second guide can be engaged within the proximal cap or the vessel wall adjacent to the proximal cap and advanced, in an antegrade direction, until its distal end is near or axially overlaps a distal end of the first guide. A first vessel lumen, formed by advancement of the first guide, and a second vessel lumen, formed by advancement of the second guide, can be connected by inflating a balloon positioned at or near the distal end of the second guide. The distal end of the first guide can be received by a passage of the inflated balloon, the balloon can be subsequently deflated to collapse the passage and clamp a passage wall against the first guide's distal end, and the balloon and first guide can be pulled into an antegrade guide catheter.

24 Claims, 8 Drawing Sheets

(52) U.S. Cl.
CPC .............. *A61B 2017/22041* (2013.01); *A61B 2017/22042* (2013.01); *A61B 2017/22044* (2013.01); *A61B 2017/22062* (2013.01); *A61B 2017/22067* (2013.01); *A61B 2017/22095* (2013.01)

(58) Field of Classification Search
CPC ........... A61B 2017/22042; A61B 2017/22062; A61B 2017/22044; A61B 2017/22038; A61B 2017/22095
See application file for complete search history.

(56) References Cited

U.S. PATENT DOCUMENTS

| | | | |
|---|---|---|---|
| 4,944,745 A | 7/1990 | Sogard et al. | |
| 5,047,045 A | 9/1991 | Arney et al. | |
| 5,087,247 A | 2/1992 | Horn et al. | |
| 5,181,911 A | 1/1993 | Shturman | |
| 5,195,969 A | 3/1993 | Wang et al. | |
| 5,226,888 A | 7/1993 | Arney | |
| 5,226,889 A | 7/1993 | Sheiban | |
| 5,252,159 A | 10/1993 | Arney | |
| 5,257,974 A | 11/1993 | Cox | |
| 5,290,247 A | 3/1994 | Crittenden | |
| 5,290,310 A | 3/1994 | Makower et al. | |
| 5,368,566 A | 11/1994 | Crocker | |
| 5,370,617 A | 12/1994 | Sahota | |
| 5,370,691 A | 12/1994 | Samson | |
| 5,421,826 A | 6/1995 | Crocker et al. | |
| 5,439,445 A | 8/1995 | Kontos | |
| 5,470,314 A | 11/1995 | Walinsky | |
| 5,505,702 A | 4/1996 | Arney | |
| 5,536,250 A | 7/1996 | Klein et al. | |
| 5,545,135 A | 8/1996 | Iacob et al. | |
| 5,549,552 A | 8/1996 | Peters et al. | |
| 5,554,119 A | 9/1996 | Harrison et al. | |
| 5,556,382 A | 9/1996 | Adams | |
| 5,558,642 A | 9/1996 | Schweich et al. | |
| 5,569,184 A | 10/1996 | Crocker et al. | |
| 5,613,948 A | 3/1997 | Avellanet | |
| 5,643,171 A | 7/1997 | Bradshaw et al. | |
| 5,649,978 A | 7/1997 | Samson | |
| 5,690,642 A | 11/1997 | Osborne et al. | |
| 5,716,340 A | 2/1998 | Schweich et al. | |
| 5,720,723 A | 2/1998 | Adams | |
| 5,738,667 A | 4/1998 | Solar | |
| 5,800,450 A | 9/1998 | Lary et al. | |
| 5,855,546 A | 1/1999 | Hastings et al. | |
| 5,879,369 A | 3/1999 | Ishida | |
| 5,882,290 A | 3/1999 | Kume | |
| 5,891,154 A | 4/1999 | Loeffler | |
| 5,935,114 A | 8/1999 | Jang et al. | |
| 5,961,490 A | 10/1999 | Adams | |
| 6,083,215 A | 7/2000 | Milavetz | |
| 6,110,097 A | 8/2000 | Hastings et al. | |
| 6,187,014 B1 | 2/2001 | Goodin et al. | |
| 6,190,355 B1 | 2/2001 | Hastings | |
| 6,245,040 B1 | 6/2001 | Inderbitzen et al. | |
| 6,361,529 B1 | 3/2002 | Goodin et al. | |
| 6,371,971 B1 | 4/2002 | Tsugita et al. | |
| 6,379,319 B1 | 4/2002 | Garibotto et al. | |
| 6,387,119 B2* | 5/2002 | Wolf .................... A61F 2/2493 | 128/898 |
| 6,503,224 B1 | 1/2003 | Forman et al. | |
| 6,506,180 B1 | 1/2003 | Lary | |
| 6,673,090 B2 | 1/2004 | Root et al. | |
| 6,945,957 B2 | 9/2005 | Freyman | |
| 6,945,977 B2 | 9/2005 | Demarais et al. | |
| 7,147,655 B2 | 12/2006 | Chermoni | |
| 7,232,452 B2 | 6/2007 | Adams et al. | |
| 7,517,352 B2* | 4/2009 | Evans .................... A61B 17/22 | 606/167 |
| 7,563,247 B2 | 7/2009 | Maguire et al. | |
| 7,918,859 B2 | 4/2011 | Katoh et al. | |
| 7,938,819 B2 | 5/2011 | Kugler et al. | |
| 8,048,032 B2 | 11/2011 | Root et al. | |
| 8,167,902 B2 | 5/2012 | Quinn et al. | |
| 8,172,772 B2 | 5/2012 | Zwolinski et al. | |
| 8,241,311 B2* | 8/2012 | Ward .............. A61B 17/320783 | 128/898 |
| 8,323,261 B2* | 12/2012 | Kugler ................ A61B 17/221 | 604/509 |
| 8,430,845 B2 | 4/2013 | Wahr et al. | |
| 8,469,925 B2 | 6/2013 | Rowe et al. | |
| 8,486,014 B2 | 7/2013 | Kelly et al. | |
| 8,636,712 B2* | 1/2014 | Kugler ................ A61B 17/221 | 604/509 |
| 8,696,699 B2 | 4/2014 | Chomas et al. | |
| 8,961,494 B2* | 2/2015 | Kugler ................ A61B 17/221 | 604/509 |
| 8,974,482 B2 | 3/2015 | Shriver | |
| 9,301,777 B2* | 4/2016 | Silvestro .............. A61B 17/3478 | |
| 9,308,356 B2* | 4/2016 | Silvestro .............. A61B 17/3415 | |
| 9,364,642 B2* | 6/2016 | Sina .................. A61M 25/0155 | |
| 9,446,222 B2* | 9/2016 | Silvestro ............... A61M 29/02 | |
| 9,878,128 B2* | 1/2018 | Kugler ................ A61B 17/2256 | |
| 9,968,763 B2 | 5/2018 | Root et al. | |
| 10,172,632 B2* | 1/2019 | Morero .................. A61B 17/22 | |
| 2002/0169458 A1* | 11/2002 | Connors, III .......... A61B 17/22 | 606/108 |
| 2003/0032920 A1 | 2/2003 | Wantink | |
| 2003/0040704 A1 | 2/2003 | Dorros et al. | |
| 2003/0050600 A1 | 3/2003 | Ressemann et al. | |
| 2003/0093090 A1 | 5/2003 | McGuckin et al. | |
| 2003/0120195 A1 | 6/2003 | Milo et al. | |
| 2003/0233068 A1 | 12/2003 | Jayaraman | |
| 2004/0049152 A1* | 3/2004 | Nayak .............. A61B 17/12109 | 604/96.01 |
| 2004/0093008 A1 | 5/2004 | Zamore | |
| 2004/0142704 A1 | 7/2004 | Scholz | |
| 2004/0230178 A1 | 11/2004 | Wu | |
| 2005/0075662 A1 | 4/2005 | Pedersen et al. | |
| 2005/0154447 A1 | 7/2005 | Goshgarian | |
| 2005/0177130 A1 | 8/2005 | Konstantino et al. | |
| 2005/0209559 A1 | 9/2005 | Thornton et al. | |
| 2005/0209678 A1 | 9/2005 | Henkes et al. | |
| 2005/0267442 A1 | 12/2005 | Oepen | |
| 2006/0074474 A1* | 4/2006 | Theron ............ A61B 17/12136 | 623/1.11 |
| 2006/0142704 A1 | 6/2006 | Lentz | |
| 2006/0200191 A1 | 9/2006 | Zadno-Azizi | |
| 2006/0210605 A1 | 9/2006 | Chang et al. | |
| 2006/0224176 A1 | 10/2006 | Fung et al. | |
| 2007/0093779 A1* | 4/2007 | Kugler ................ A61B 17/221 | 604/509 |
| 2007/0093781 A1* | 4/2007 | Kugler ................ A61B 17/221 | 604/510 |
| 2007/0208368 A1 | 9/2007 | Katoh et al. | |
| 2008/0058836 A1 | 3/2008 | Moll et al. | |
| 2008/0082051 A1 | 4/2008 | Miller et al. | |
| 2008/0114390 A1 | 5/2008 | Guinan | |
| 2008/0200896 A1 | 8/2008 | Shmulewitz et al. | |
| 2008/0306499 A1 | 12/2008 | Katoh et al. | |
| 2008/0312681 A1 | 12/2008 | Ansel et al. | |
| 2009/0105641 A1 | 4/2009 | Nissl | |
| 2009/0124899 A1 | 5/2009 | Jacobs et al. | |
| 2009/0177259 A1 | 7/2009 | Ning et al. | |
| 2009/0254114 A1 | 10/2009 | Hirszowicz et al. | |
| 2009/0264826 A1 | 10/2009 | Thompson | |
| 2011/0009818 A1 | 1/2011 | Goff | |
| 2011/0264039 A1 | 10/2011 | Thielen et al. | |
| 2012/0136382 A1* | 5/2012 | Kugler ................ A61B 17/221 | 606/185 |
| 2012/0245520 A1 | 9/2012 | Kelly et al. | |
| 2012/0259214 A1 | 10/2012 | Solar et al. | |
| 2012/0289983 A1 | 11/2012 | Ogata et al. | |
| 2013/0072957 A1* | 3/2013 | Anderson ............ A61M 25/104 | 606/194 |
| 2013/0103070 A1* | 4/2013 | Kugler ................ A61B 17/221 | 606/185 |
| 2013/0178887 A1 | 7/2013 | Rosenschein et al. | |

(56) References Cited

U.S. PATENT DOCUMENTS

| | | | |
|---|---|---|---|
| 2013/0204278 A1* | 8/2013 | Cully | A46B 3/18 |
| | | | 606/159 |
| 2013/0261729 A1 | 10/2013 | Gillick et al. | |
| 2013/0274674 A1 | 10/2013 | Fischell et al. | |
| 2013/0317485 A1 | 11/2013 | Lupton | |
| 2014/0018773 A1 | 1/2014 | Wang et al. | |
| 2014/0025086 A1 | 1/2014 | Rottenberg et al. | |
| 2014/0031918 A1 | 1/2014 | Newell et al. | |
| 2014/0171958 A1 | 6/2014 | Baig | |
| 2014/0277068 A1* | 9/2014 | Kugler | A61B 17/2256 |
| | | | 606/194 |
| 2015/0032148 A1 | 1/2015 | Golan | |
| 2015/0051633 A1* | 2/2015 | Sina | A61M 25/0074 |
| | | | 606/194 |
| 2015/0196360 A1 | 7/2015 | Grantham et al. | |
| 2015/0209065 A1 | 7/2015 | Dahm et al. | |
| 2016/0008584 A1 | 1/2016 | Root et al. | |
| 2016/0045219 A1* | 2/2016 | Guala | A61M 25/0194 |
| | | | 606/185 |
| 2016/0066932 A1 | 3/2016 | Root et al. | |
| 2016/0066933 A1 | 3/2016 | Root et al. | |
| 2016/0074627 A1* | 3/2016 | Cottone | A61M 25/0068 |
| | | | 604/510 |
| 2016/0250448 A1* | 9/2016 | Copeta | A61M 25/0194 |
| | | | 606/159 |
| 2017/0050003 A1 | 2/2017 | Root et al. | |
| 2017/0079671 A1* | 3/2017 | Morero | A61B 17/22 |
| 2017/0143355 A1 | 5/2017 | Nicholson | |
| 2018/0333162 A1* | 11/2018 | Saab | A61B 17/22 |

FOREIGN PATENT DOCUMENTS

| | | |
|---|---|---|
| JP | 2011505918 A | 3/2011 |
| JP | 6097447 | 2/2017 |
| JP | 6326517 B2 | 4/2018 |
| WO | 1993007929 A1 | 4/1993 |
| WO | 1994026206 A1 | 11/1994 |
| WO | 1997032626 A2 | 9/1997 |
| WO | 1998055179 A1 | 12/1998 |
| WO | 2000020064 A1 | 4/2000 |
| WO | 2000023139 A1 | 4/2000 |
| WO | 2001097697 A1 | 12/2001 |
| WO | 2004039290 A1 | 5/2004 |
| WO | 2005027995 A2 | 3/2005 |
| WO | 2009122300 A2 | 10/2009 |
| WO | 2011129915 A2 | 10/2011 |
| WO | 2012037507 A1 | 3/2012 |
| WO | 2012141749 A1 | 10/2012 |
| WO | 2014037836 A1 | 3/2014 |
| WO | 2014055547 A1 | 4/2014 |
| WO | 2015105930 A1 | 7/2015 |
| WO | 2016025324 A1 | 2/2016 |

OTHER PUBLICATIONS

Final Rejection dated Aug. 8, 2018, in U.S. Appl. No. 14/850,095.
Response to Final Rejection, filed Sep. 1, 2017, in related U.S. Appl. No. 14/850,095.
Response to Office Action, filed Jul. 25, 2017, in European Application No. 15770712.6.
Office Action dated Oct. 5, 2017, in related European Application No. 15770712.6 filed Sep. 10, 2015.
Response to Office Action filed Dec. 4, 2017, in related European Application No. 15770712.6 filed Sep. 10, 2015.
Japanese Office Action dated Dec. 19, 2017, in Japanese Application No. 2017-028336.
Japanese response to office action filed Mar. 16, 2018, in Japanese Application No. 2017-028336.
Response to Office Action filed Feb. 28, 2018 in corresponding U.S. Appl. No. 15/296,183.
European Office Action dated Mar. 29, 2017, in related application EP 15770712.6 filed Sep. 10, 2015.
Final Rejection dated May 3, 2017, in U.S. Appl. No. 14/850,095.
Non-final office action dated Mar. 22, 2017, in U.S. Appl. No. 14/850,095, filed Sep. 10, 2015.
Response filed Apr. 7, 2017, to non-final office action of Mar. 22, 2017, in U.S. Appl. No. 14/850,095.
Office Action dated Sep. 9, 2016, in connection with U.S. Appl. No. 14/850,095.
Response to Office Action, filed Sep. 16, 2016, in connection with U.S. Appl. No. 14/850,095.
Final Rejection dated Oct. 6, 2016, in connection with U.S. Appl. No. 14/850,095.
Amendment After Final, filed Oct. 14, 2016, in connection with U.S. Appl. No. 14/850,095.
Advisory Action dated Oct. 27, 2016, in connection with U.S. Appl. No. 14/850,095.
Request for Continued Examination filed Nov. 4, 2016, in connection with U.S. Appl. No. 14/850,095.
Response to Office Action, filed Nov. 1, 2016, in corresponding Japanese Patent Application 2016-515958, including English translation of amended claims.
U.S. Appl. No. 14/850,095, filed Sep. 10, 2015, Perfusion Catheters and Related Methods.
U.S. Appl. No. 15/296,183, filed Oct. 18, 2016, Perfusion Catheters and Related Methods.
European Search Report and Search Opinion in EP18177601 A, dated Oct. 12, 2018.
Notice of Allowance dated Oct. 25, 2018, in U.S. Appl. No. 14/850,095.
Office Action dated Feb. 23, 2018, in U.S. Appl. No. 14/850,095, filed Sep. 10, 2015.
Office Action dated Feb. 23, 2018, in U.S. Appl. No. 15/296,183, filed Oct. 18, 2016.
Response to Office Action, filed Jun. 22, 2018, in U.S. Appl. No. 14/850,095.
Spectranetics. Quick-Cross Capture Guidewire Retriever [brochure]. Colorado Springs, CO: Spectranetics Corporation, 2013 [retrieved on Sep. 3, 2014]. Retrieved from the Internet: <http://www.spectranetics.com/wp-content/uploads/2013/01/D019438-01-QuickCrossCapture.pdf>.
International Search Report dated Nov. 24, 2015, from PCT application PCT/US2015/049356 filed Sep. 10, 2015.
Office Action dated Sep. 29, 2016, in Japanese Patent Application 2016-515958 filed Sep. 10, 2015 (PCT filing date).
Written Opinion dated Nov. 24, 2015, from PCT application PCT/US2015/049356 filed Sep. 10, 2015.

* cited by examiner

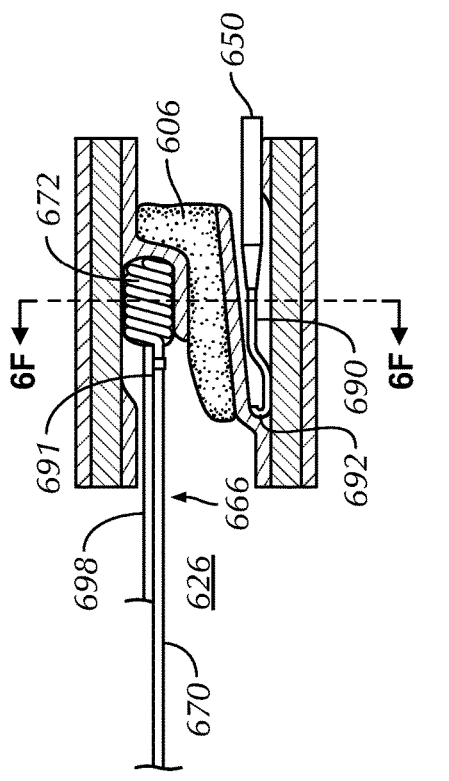
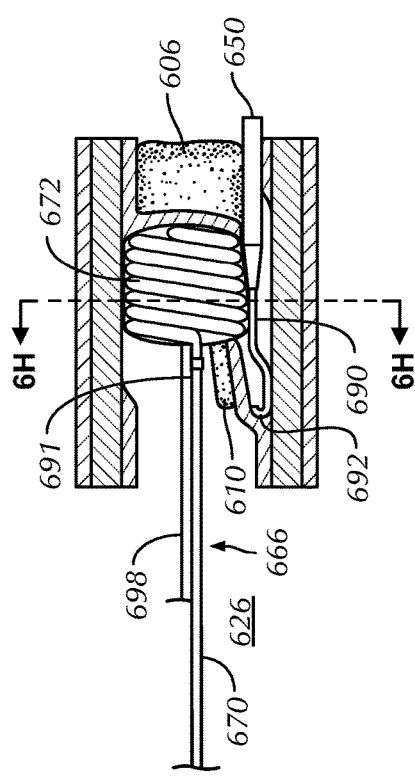
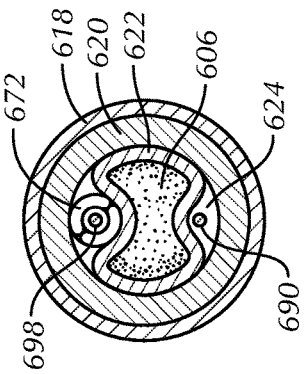
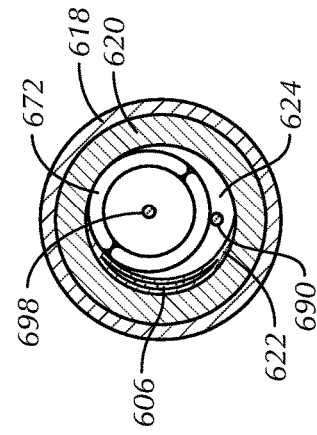
FIG. 6E
FIG. 6F
FIG. 6G
FIG. 6H

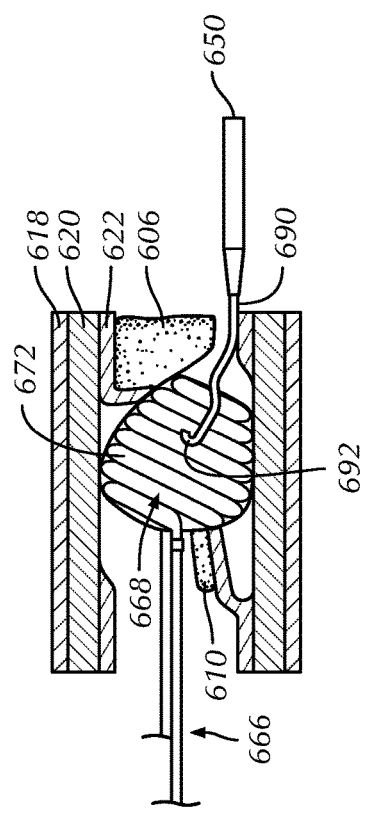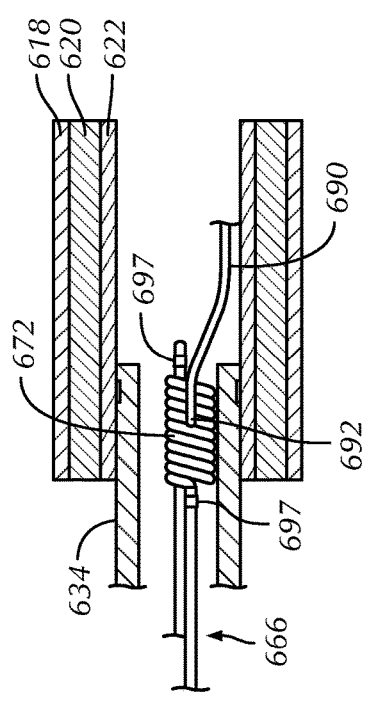
FIG. 6I
FIG. 6J

METHODS FOR FACILITATING REVASCULARIZATION OF OCCLUSION

CLAIM OF PRIORITY

This non-provisional patent document claims the benefit of priority under 35 U.S.C. § 119(e) to U.S. Provisional Patent Application Ser. No. 62/401,964, entitled "METHODS FOR FACILITATING REVASCULARIZATION OF OCCLUSION" and filed on Sep. 30, 2016, which is herein incorporated by reference in its entirety.

TECHNICAL FIELD

This patent document relates to methods for treating occluded blood vessels. More particularly, but not by way of limitation, the patent document relates to methods for facilitating revascularization of severe or chronic occlusions in blood vessels.

BACKGROUND

Atherosclerosis is a complex, progressive and degenerative condition resulting in the build-up of cholesterol and other occlusive materials, known as plaque, on the walls of blood vessels. The accumulation of plaque narrows the interior (lumen) of the vessels reducing blood flow. Plaque occurs in blood vessels in several different forms and can be located in many different anatomies throughout a vascular system. For example, an occluded vessel may lie in the blood vessels of the heart (coronary arteries) or in the peripheral vasculature supplying the extremities or other vital organ systems. Plaque can vary in composition, with portions that are hard and fibrous, known as calcified plaque, and other portions that are soft and fatty.

Over time, plaque deposits can become large enough to substantially reduce or totally occlude blood flow through a vessel, which can lead to symptoms associated with low blood flow, including cardiac arrest, stroke, or tissue or organ necrosis. Chronic total occlusions (CTOs) are one type of plaque deposit, usually including calcified plaque portions, which block the blood path through the affected vessel. To treat plaque deposits and improve or resolve low blood flow symptoms, it is desirable to restore or improve blood flow through the affected vessel.

Chronic total occlusions have historically been treated by performing a bypass procedure, where an autologous or synthetic blood vessel is anastomotically attached to locations on the native vessel upstream and downstream of the occlusion. While effective, such bypass procedures are quite traumatic to the patient and can become blocked over time. A more recent procedure for treating CTOs and other severe occlusions is percutaneous transluminal coronary angioplasty (PTCA). During a PTCA procedure, a small incision is (typically) made in the groin. A guide catheter is introduced into the femoral artery over a guidewire and advanced toward the occlusion. This is called an antegrade approach. A number of devices have been developed or used for the percutaneous interventional treatment of CTOs, such as stiffer guidewires, atherectomy devices, drills, drug eluting stents, and re-entry catheters.

A factor that is determinative of whether a treating clinician can successfully revascularize a CTO is the clinician's ability to advance a suitable guidewire from a position within the true lumen of a vessel proximal to the occlusion, across the CTO occlusion (i.e., either through the occlusion or around it), and then back into the true lumen of the vessel at a location distal to the occlusion. Once the guidewire is maneuvered into place by being passed into and across the occlusion, it can act as a rail for positioning a subsequent treatment device, such as a balloon-tipped angioplasty catheter. When appropriately positioned within the occlusion, the balloon can be inflated to apply radial pressure and compress the plaque deposit to increase blood flow through the affected vessel. Commonly, a stent is subsequently placed.

Overview

The present inventor recognizes that it is desirable to have techniques for simplifying the revascularization of a CTO or other severe occlusion after attempts to cross the occlusion in a true lumen-to-true lumen manner have failed. The present inventor further recognizes that in many severe blockages, including CTOs, an antegrade approach is unsuccessful in crossing the occlusion. More specifically, the present inventor recognizes that there is a need for an easier and simpler way of connecting with and capturing a retrograde-delivered device (i.e., a device delivered in a direction that is against blood flow) after it is maneuvered across an occlusion. It is these recognitions that led to the methods disclosed in the present patent document.

A method for facilitating revascularization of an occlusion in a blood vessel can include engaging a first guide within a vessel wall adjacent to a distal cap of an occlusion and advancing the first guide, in a retrograde direction, to a subintimal position near a proximal cap of the occlusion. A second guide can be engaged within the proximal cap or the vessel wall adjacent to the proximal cap and advanced, in an antegrade direction, until its distal end is near or axially overlaps a distal end of the first guide. The first guide can include one or both of a retrograde-delivered guidewire or specialty catheter, and the second guide can include one or both of an antegrade-delivered guidewire or specialty catheter. A first vessel lumen, formed by advancement of the first guide, and a second vessel lumen, formed by advancement of the second guide, can be connected by inflating a balloon positioned at or near the distal end of the second guide. The balloon can include a tube coiled in a helical manner around a central axis into a series of windings, with adjacent windings stacked against and bonded to each other, and, when inflated, can form a passage. The distal end of the first guide can be received by the passage, the balloon can be subsequently deflated to collapse the passage and clamp a passage wall against the first guide's distal end, and the balloon and first guide can be pulled into an antegrade guide catheter.

These and other examples and features of the present methods will be set forth, at least in part, in the following Detailed Description. This Overview is intended to provide non-limiting examples of the present subject matter—it is not intended to provide an exclusive or exhaustive explanation. The Detailed Description below is included to provide further information about the present methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in the present patent document.

FIGS. 6A-J illustrate sequential views of a method of advancing a retrograde-delivered guidewire across an occlusion and receiving and capturing its distal end using a specialized balloon catheter on an antegrade side of the occlusion, as constructed in accordance with at least embodiment.

Figure 1:
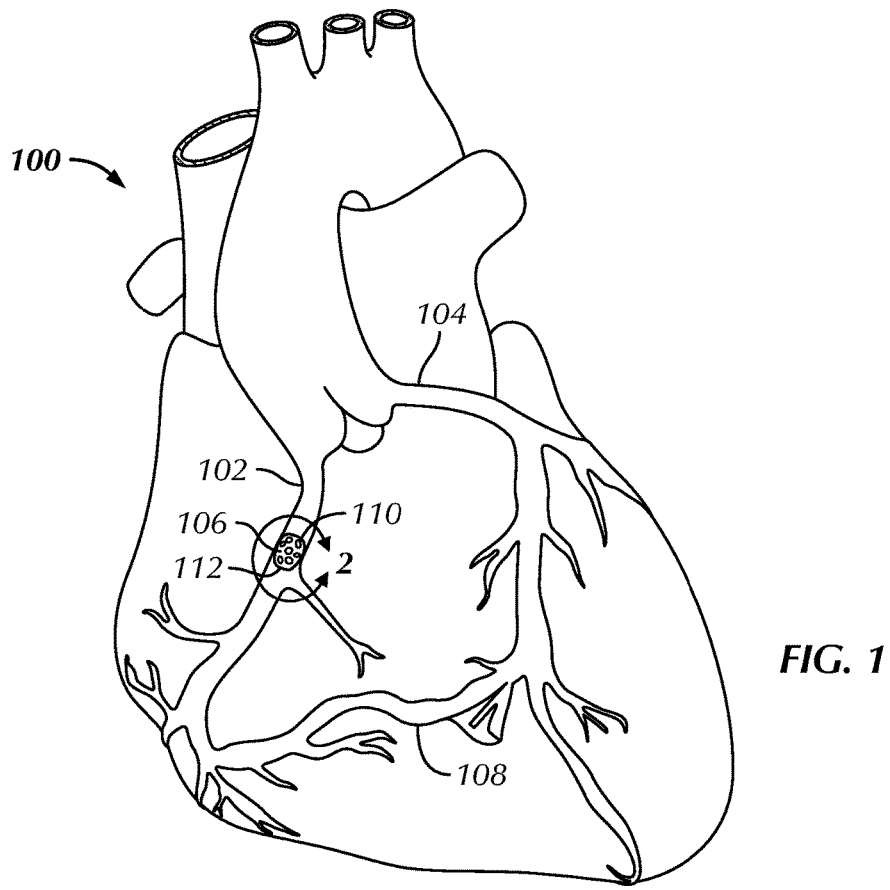
FIG. 1 illustrates a schematic view of a heart and an occlusion located within a coronary artery.

The drawing figures are not necessarily to scale. Certain features and components may be shown exaggerated in scale or in schematic form and some details may not be shown in the interest of clarity and conciseness.

DETAILED DESCRIPTION

Introduction:

The present subject matter provides methods for the treatment of CTOs and other severe occlusions using a combined antegrade and retrograde approach. A retrograde-delivered guidewire can be engaged within a vessel wall adjacent to a distal cap of an occlusion and advanced to a subintimal position near a proximal cap of the occlusion. A specialized balloon catheter, including, for example, a helically coiled tube and an elongate shaft eccentrically positioned relative to the helically coiled tube, can be guided over an antegrade-delivered guidewire and inflated to provide an enlarged antegrade space for the retrograde-delivered guidewire to connect with. Upon reaching the enlarged space, a distal end of the retrograde-delivered guidewire can be received by a passage of the inflated balloon, and the balloon can be subsequently deflated to capture the guidewire against a wall of the collapsed passage. Together, the balloon catheter and the retrograde-delivered guidewire can be pulled into an antegrade guide catheter to complete a true lumen-to-true lumen connection across the occlusion. The disclosed methods are particularly beneficial in crossing coronary total occlusions but may also be useful in other vessels, including peripheral arteries and veins.

Coronary CTO:

FIG. 1 illustrates a schematic view of a heart 100, including a right main coronary artery 102 and a left main coronary artery 104. Branches formed off of these main coronary arteries 102, 104 supply oxygenated blood to the various parts of the heart 100. An occlusion 106 is shown in a branch of the right main coronary artery 102. The occlusion 106 can be caused by an embolus, a thrombus, or by other types of materials.

In some instances, the extent to which the artery's lumen is narrowed at the occlusion 106 is so severe that the lumen is completely or nearly completely obstructed, which may be described as a total occlusion. Total or near-total occlusions in arteries can prevent all or nearly all of the blood flow through the affected arteries. If the occlusion 106 has been established for a long period of time, the lesion may be referred to as a CTO. Collateral pathways 108 often develop as a result of a CTO providing some, but not adequate, perfusion to heart tissue. Common symptoms of a CTO include, but are not limited to, chest pain, pressure or tightness, shortness of breath, dizziness and fatigue, nausea, pain in the upper body and arm, and/or rapid or irregular heartbeat. Chronic total occlusions can occur in coronary as well as peripheral arteries.

Chronic total occlusions are often characterized by extensive plaque formation and typically include fibrous caps 110, 112 surrounding softer plaque material. The fibrous caps 110, 112 may present surfaces that are difficult to penetrate with a conventional guidewire. Specific methods for revascularizing a coronary artery obstructed by a CTO or other severe occlusion are discussed in this patent document. Once the artery has been revascularized, blood flows through the artery to the affected area of the heart 100.

Figure 2:
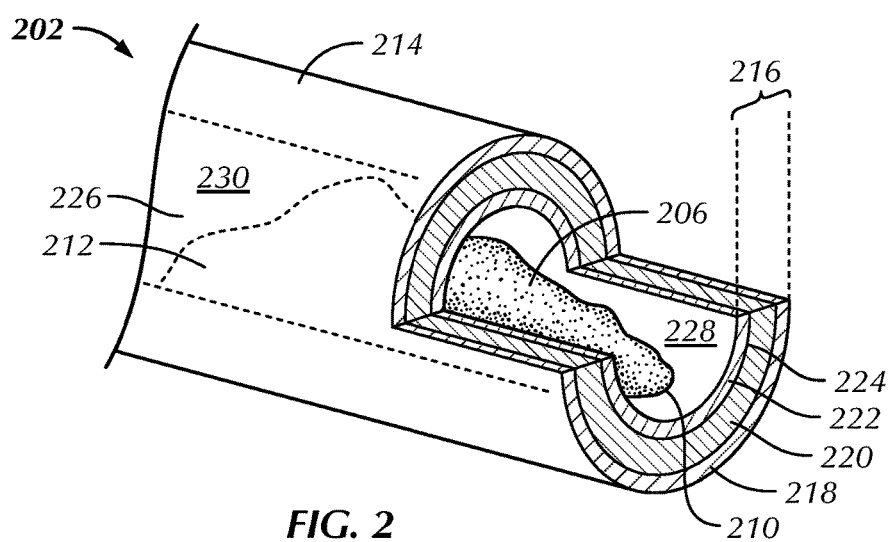
FIG. 2 illustrates a schematic view of a coronary artery containing an occlusion and the artery's intimal, medial and adventitial wall layers.

Arterial Anatomy:

FIG. 2 is a partial sectional view of an artery 202 having a wall 214 comprising three layers 216. The outermost layer of the wall is the adventitia 218, and the innermost layer of the wall is the intima 222. The tissues extending between the intima 222 and the adventitia 218 can be collectively referred to as the media 220. The adventitial layer 218 has, on average, about three times higher ultimate tensile strength than the medial and intimal layers 220, 222. The transition between the external most portion of the intima 222 and the internal most portion of the media 220 is sometimes referred to as the subintimal space 224. It is the subintimal space 224 through which the guidewires, specialty catheters, and other treatment devices of the present methods can pass when crossing a total or near-total occlusion.

The intima 222 defines a true lumen 226 of the artery 202. In FIG. 2, an occlusion 206 is shown blocking the true lumen 226. The occlusion 206 divides the true lumen 226 of the artery into a proximal segment 228 and a distal segment 230, and can comprise a proximal fibrous cap 210, a distal fibrous cap 212 and an occlusion body therebetween. In the combined antegrade and retrograde treatment approach, the distal cap 212 is approached from a retrograde direction, and the proximal cap 210 is approached from an antegrade direction.

The anatomy of a venous wall is similar to the anatomy of the arterial wall with two primary exceptions. First, arterial walls are thicker than venous walls to withstand higher pressures produced from heartbeats. Second, an endothelium layer on an inner surface of the intima of a vein includes one or more valves. Since blood in veins flows against gravity, the valves prevent backflow and keep blood moving toward the heart. The similarities between venous and arterial wall anatomies allow the present methods to be used in a similar manner in both vessel types.

Dual Catheter Angiography:

Bi-lateral contrast injections are needed to fully visualize a CTO or other severe occlusion. Guide catheters positioned on each side of the occlusion can be used to deliver timed retrograde and antegrade injections while multiple angiographic views are taken. The views can provide information about the occlusion's length—the distance from its proximal cap to its distal cap—and illustrate the vasculature best suited to reach such caps.

Figure 3:
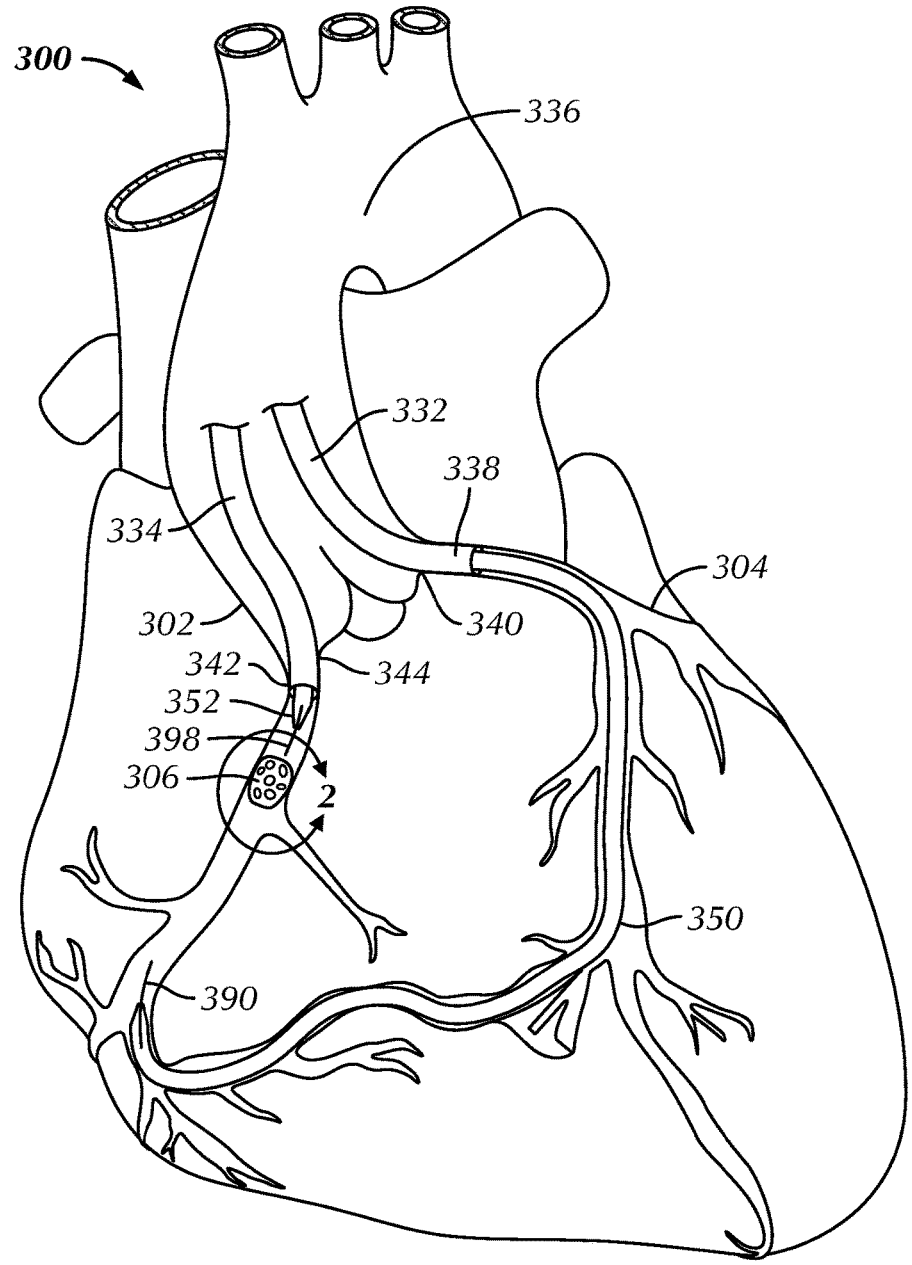
FIG. 3 illustrates a schematic view of a bi-lateral arrangement of guide catheters positioned within a heart for delivering contrast to allow visualization of an occlusion.

FIG. 3 schematically illustrates a bi-lateral arrangement of first and second guide catheters 332, 334 positioned within a heart 300 for delivering contrast. The first (retrograde) guide catheter 332 can extend through the aortic arch 336 and have its distal end 338 introduced into a blood vessel at a location downstream of an occlusion 306, such as at an ostium 340 to the left main coronary artery 304. The second (antegrade) guide catheter 334 can extend through the aortic arch 336 and have its distal end 342 introduced into a blood vessel at a location upstream of the occlusion 306, such as at an ostium 344 to the right main coronary artery 302. A variety of different catheter shapes are available which generally facilitate access to the coronary ostia. In addition to being used as injection catheters, the first and second guide catheters 332, 334 can be used for delivery of guidewires 390, 398, specialty catheters 350, 352, and other treatment devices, as further discussed below. Optionally, a guide extension catheter, such as the GUIDELINER extension catheter commercially available from Vascular Solutions, Inc. (Minneapolis, Minn.), can be advanced through a lumen of the first or second guide catheters 332, 334 and have its distal end positioned nearer an end cap of the occlusion 306 than the distal end of the guide catheters.

Figure 4A:
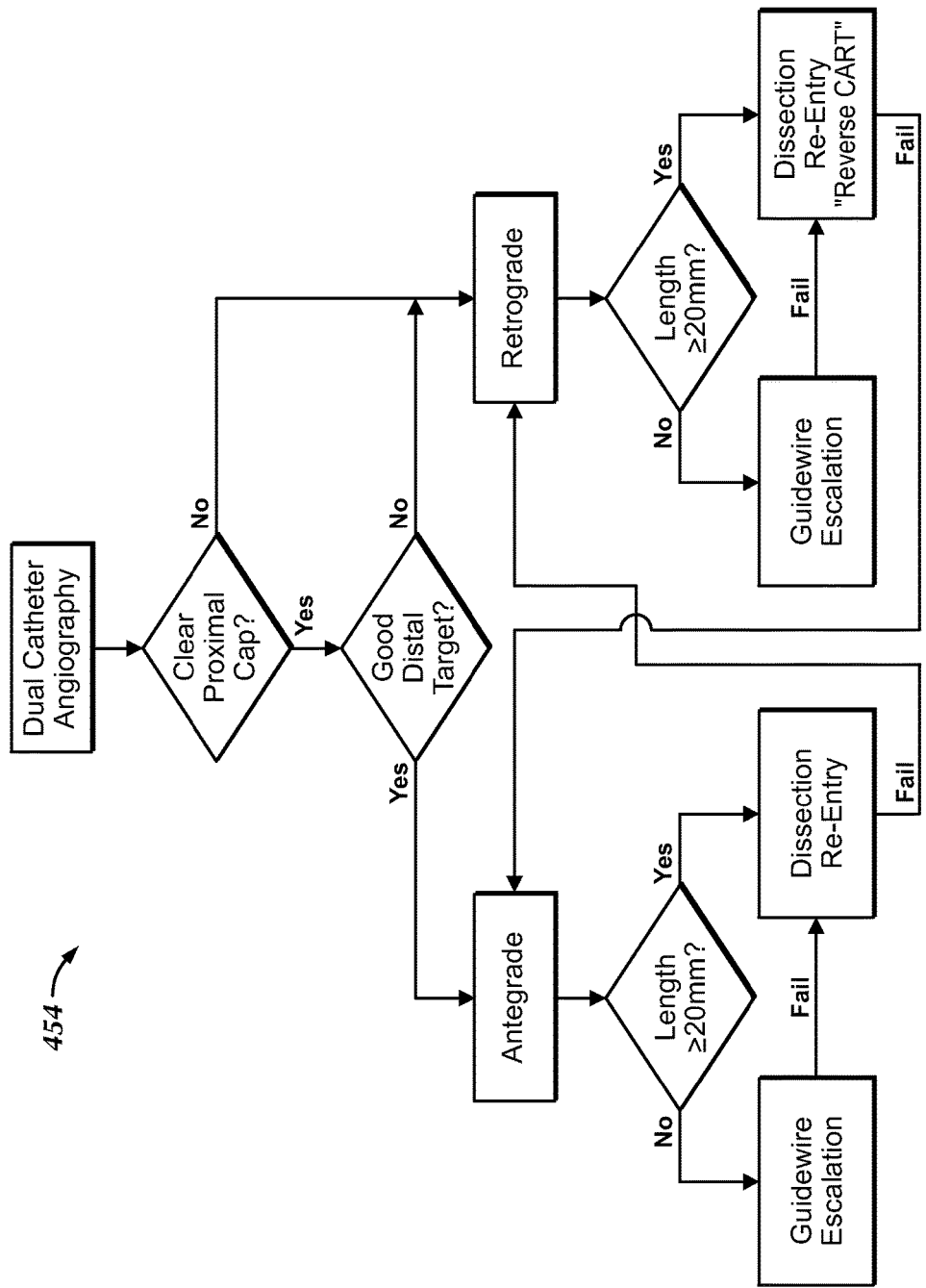
FIGS. 4A-B illustrate antegrade and retrograde options for treating an occlusion within a vessel.
Figure 4B:
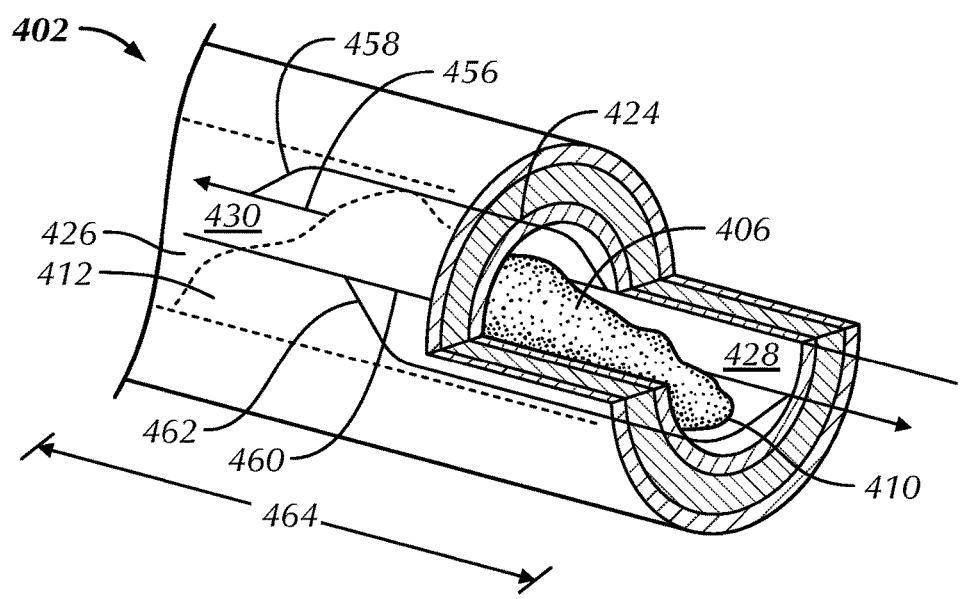

Treatment Algorithm and Pathways for CTOs:

To date, there is no consensus on how best to treat CTOs or other severe occlusions after attempts with conventional guidewires have failed. Different strategies and specific devices for CTOs have been developed; however, none of these strategies or devices provides satisfactory results for the most challenging of the CTOs. FIGS. 4A-B illustrate antegrade and retrograde options for treating an occlusion 406 within a vessel 402. Specifically, FIG. 4A illustrates an algorithm 454, in flow diagram form, for systematical treating the occlusion percutaneously, and FIG. 4B illustrates various antegrade and retrograde pathways 456, 458, 460, 462 for crossing the occlusion 406. The treatment algorithm 454 can facilitate occlusion crossing by establishing a strategy of techniques based on angiographic findings and physiologic features of the patient and the target occlusion 406. The algorithm 454 allows treating clinicians to systematically move from one strategy to another to facilitate occlusion crossing success and procedural efficiency.

If bi-lateral contrast injections illustrate that the occlusion 406 has clear proximal and distal caps 410, 412, the antegrade approach 456, 458 can be turned to first and, if the length 464 of the occlusion 406 is less than about 20 millimeters (mm), guidewire escalation can be attempted. Depending on the type and the composition of the occlusion 406, it may be difficult to successfully penetrate the occlusion using standard guidewire techniques. In particular, the proximal cap 410 of the occlusion 406 may be composed of dense, fibrous tissue with fibrocalcific regions. It may be necessary to use a guidewire of sufficient rigidity to successfully penetrate the proximal cap 410. Also, it may generally be necessary to apply substantial force in order to penetrate the proximal cap of the occlusion and recanalize the body vessel by going true lumen proximally 428 to true lumen distally 430 without entering the subintimal space. An example escalation of guidewires can be: (1) attempting to cross the occlusion 406 with a soft tapered polymer jacketed guidewire (e.g., the FIELDER XT or FIELDER XT-A guidewires commercially available from Abbott Vascular (Abbott Park, Ill.)), (2) attempting to cross the occlusion 406 with a stiffer polymer jacketed guidewire (e.g., the PILOT 200 guidewire commercially available from Abbott Vascular), and (3) attempting to cross the occlusion 406 with a stiff penetration guidewire (e.g., the CONFIANZA PRO 12 guidewire commercially available from Abbott Vascular).

In some instances, such as where the occlusive matter is soft or where the occlusion 406 is less than total, the guidewire can be pushed through the occlusive matter itself, thereby allowing the guidewire to remain within the vessel's true lumen 426. However, in other cases, such as where the vessel 402 is totally occluded by hard, calcified atherosclerotic plaque and/or has a length 464 greater than or equal to about 20 mm, the guidewire may tend to deviate to one side of the occlusion 406 and penetrate through the intima of the vessel, thereby creating a neo-lumen in the subintimal space 424 (false lumen). In these cases, the distal end of the guidewire may be advanced to a position distal to the lesion but remains entrapped within the subintimal space 424. In such instances, it is then necessary to divert or steer the guidewire from the subintimal space back into the true lumen 426 of the artery at a location distal to the CTO lesion, such as by using the STINGRAY catheter commercially available from Boston Scientific Corporation (Marlborough, Mass.).

In many severe blockages, particularly where the occlusion 406 has ambiguous proximal and distal caps, the antegrade approach 456, 458 is unsuccessful in crossing the occlusion 406. Consequently, an adjunctive technique to improve procedural success rates and reduce procedural time has been developed. This procedure involves using existing natural connections provided by body systems, such as via marginal branches or collateral pathways that connect major vessels. These natural pathways enable the occlusion 406 to be approached with devices from the retrograde direction. The main difficulty using the retrograde approach 460, 462 is making a connection between devices on the distal end of the occlusion and the proximal end of the occlusion. Guidewire escalation can be attempted to form the connection between the true lumen on the occlusion's distal end 430 and the true lumen on the occlusion's proximal end 428. However, almost one third of all coronary CTO lesions are longer than 20 mm in length 464 and guidewire escalation crossing is typically unsuccessful. In such situations, the present methods and devices illustrated and described in FIGS. 5A-B and 6A-J for passing the occlusion 406 using the subintimal space 424 outside of the vessel's true lumen 426 and regaining entry to the true lumen proximal of the occlusion can be turned to.

The pathways for crossing the occlusion 406 are the same independent of the use of the antegrade approach 456, 458 or the retrograde approach 460, 462, as illustrated in FIG. 4B. Guidewires or other treatment devices either find a true lumen pathway 456, 460 via wire escalation or find a false lumen pathway 458, 462 into the subintimal space 424.

Figures 5A, 5B:
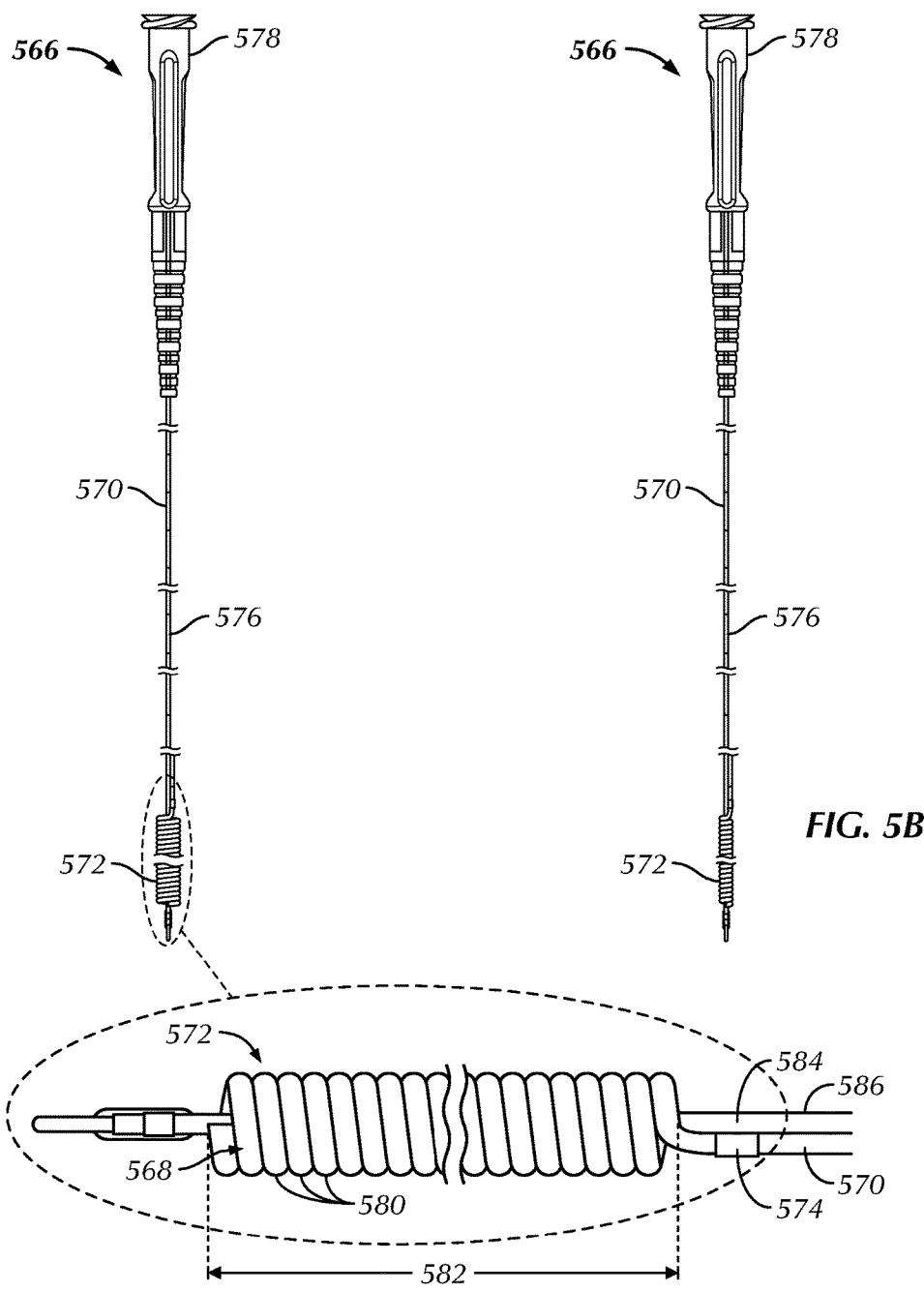
FIGS. 5A-B illustrate schematic views of a balloon catheter including a passage for receiving a retrograde-delivered guidewire, when inflated, and for capturing the retrograde-delivered guidewire, when deflated, as constructed in accordance with at least one embodiment.

Example Balloon Catheter Having Passage:

FIGS. 5A-B illustrate schematic views of a balloon catheter 566 including a passage 568 for receiving a retrograde-delivered guidewire or other device, when inflated (FIG. 5A), and for capturing the retrograde-delivered guidewire or other device, when deflated (FIG. 5B). The balloon catheter 566 can include an elongate shaft 570 and a balloon 572. A distal end portion 574 of the elongate shaft 570 can be coupled with the balloon 572 and can extend proximally therefrom for slidably positioning the balloon within and beyond a guide catheter or a guide extension catheter in use.

The elongate shaft 570 can serve two primary purposes. First, the elongate shaft 570 can transmit forces applied by a treating clinician to either advance or retract the balloon 572 during a procedure. By manipulating the elongate shaft 570, the balloon 572 can be inserted into and advanced through the guide catheter and out the distal end of the guide catheter to a treatment site. Second, the elongate shaft 570 includes a lumen 576 for providing inflation fluid to, or withdrawing inflation fluid from, the balloon 572. The lumen 576 of the elongate shaft 570 can be in fluid communication with a manifold 578, couplable to an inflation syringe, at its proximal end, and it can be in fluid communication with the interior of the balloon 572 near its distal end. The elongate shaft 570 can be eccentrically attached to a proximal end of the balloon 572 by wrapping the balloon about the shaft's distal end and affixing it thereto.

The embodiment of FIGS. 5A-B illustrates that the balloon 572 can be formed from an inflatable tube coiled in a helical or spiral manner around a central axis into a series of windings 580 (or loops), with consecutive or adjacent windings stacked against and contacting each other with substantially no space therebetween. This can ensure the windings 580 act as a unit. The inner surfaces of the windings can define the passage 568 through the open center of the helix when the coiled balloon 572 is inflated. The passage 568 can extend the full length 582 of the balloon 572 to permit receiving various lengths of a distal portion of the retrograde-delivered guidewire, for example. When the balloon 572 is deflated, its wall can collapse and flatten into a low profile configuration, which may comprise one or more folds that wrap around the distal end of the elongate shaft 570 and capture the distal portion of the received guidewire. Because the passage 568 is created through inflation of the balloon 572, the overall balloon catheter 566 can be kept to a minimal outer diameter size. This physical attribute allows the catheter 566 to be of a small diameter when it is inserted into the patient's body and maneuvered to the desired position, yet provides a relatively large passage for receiving the retrograde-delivered guidewire when the balloon 572 is inflated.

The balloon catheter 566 can optionally be provided with a guidewire lumen 584 separate from the passage 568 defined by windings of the balloon 572 and separate from the lumen 576 of the elongate shaft 570. The guidewire lumen 584 can have a length approximately equal to, or slightly longer than, the length of the passage 568 and can be positioned therein. An outer surface of a guidewire support tube 586 forming the guidewire lumen 584 can contact inner surfaces of the windings 580 of the balloon and can optionally be inset in these inner surfaces. The guidewire lumen 584 is designed to receive and facilitate tracking of a previously positioned guidewire having its distal end in position near or across a treatment site. The balloon catheter 566, and specifically the guidewire support tube 586, can be slid over the guidewire and advanced to the treatment site. Since the guidewire support tube 586 can be short compared to the total lengths of the balloon catheter 566 and the guidewire, the use of the guidewire support tube 586 as a guide permits rapid exchange of the catheter over the guidewire.

Reverse CART Using Balloon Catheter Having Passage:

With antegrade and retrograde guide catheters in place as shown in FIG. 3 and after determining, using, for example, the algorithm of FIG. 4A, that the proper treatment approach for creating a channel across a vessel occlusion is reverse controlled antegrade and retrograde tracking (reverse CART), antegrade- and retrograde-delivered guidewires can be respectively advanced to proximal and distal caps of the occlusion. The retrograde-delivered guidewire can be used to wire a collateral vessel, for example, and can be advanced to a position adjacent the distal cap with the help of a specialty catheter, such as the TURNPIKE catheter commercially available from Vascular Solutions, Inc. In various examples, the retrograde-delivered guidewire is a highly flexible and torqueable guidewire, such as the FIELDER XT or SION guidewires commercially available from Abbott Vascular, which allows access to challenging retrograde collaterals. Similarly, the antegrade-delivered guidewire can be advanced toward the proximal cap of the occlusion. FIGS. 6A-J illustrate sequential views of a method of advancing the retrograde-delivered guidewire across the occlusion and capturing its distal end using a specialized balloon catheter advanced over the antegrade-delivered guidewire and positioned in or near the proximal cap of the occlusion.

Figure 6B:
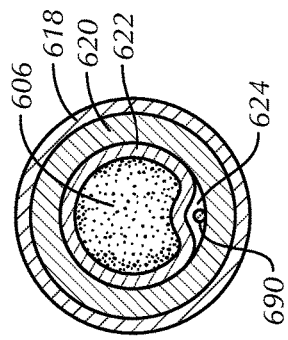

The occlusion can be crossed by first forming a track from a true lumen in the blood vessel into a subintimal space between an intimal layer and an adventitial layer of the vessel. The track can be formed so that it extends from a location distal of the occlusion to a location near the proximal cap of the occlusion. As illustrated in FIGS. 6A-B, the track 688 can be formed by advancing the retrograde-delivered guidewire 690 through the blood vessel's true lumen 626 into the subintimal space 624, typically by advancing the guidewire 690 until it encounters the occlusion 606. By continuing to advance the guidewire 690, it will usually pass into the subintimal space 624 with a prolapsed (or "knuckled") distal end 692 and can be further advanced to the desired proximal location. The blunt nature of the prolapsed distal end 692 decreases the likelihood of perforation while crossing the occlusion 606. Optionally, the retrograde-delivered guidewire used to traverse the collateral vessels can be swapped out for a polymer jacketed guidewire, such as the FIELDER XT or PILOT 200 guidewires commercially available from Abbott Vascular, which can better slide along the outer lining of the intimal layer 622.

The retrograde-delivered guidewire 690 can encounter significant resistance as it enters and/or passes through the space 624 between the intimal layer 622 and the adventitial layer 618. If resistance is encountered, a specialty catheter 650 can be used to provide column and/or torque support to the guidewire by advancing the catheter to a location just proximal of the distal end 692 of the guidewire, as shown in FIG. 6A. The guidewire 690 and the specialty catheter 650 can be incrementally advanced in the retrograde direction 662 across the occlusion 606. The specialty catheter 650 can include an elongate shaft body 694 and a tip member 696 disposed at a distal end of the shaft body. The tip member 696 can be made from a metal or a polymer and can include one or more helical threads around its outer surface or a sharpened or tapered tip to facilitate advancement through the subintimal space 624.

Figure 6D:
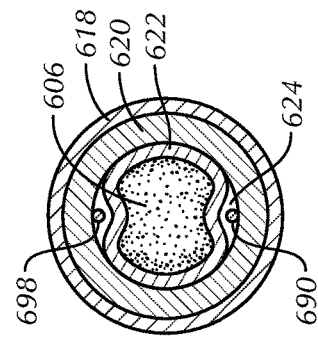
Figure 6A:
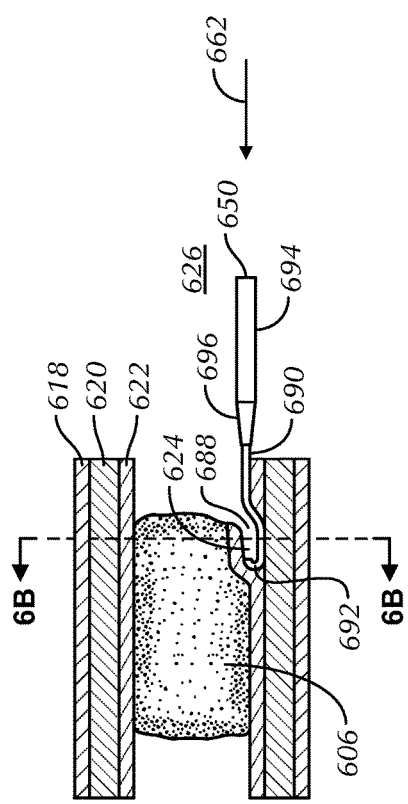
Figure 6C:
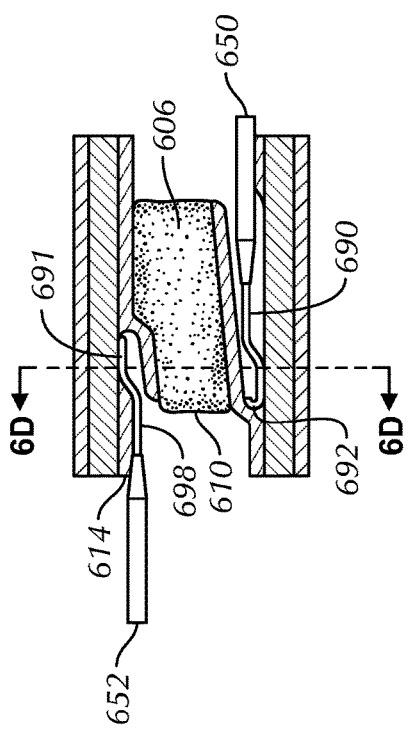

Next, as illustrated in FIGS. 6C-D, the antegrade-delivered guidewire 698, optionally supported by a specialty catheter 652, can be engaged within the vessel wall 614 or the proximal cap 610 of the occlusion 606 and advanced until its distal end 691 is near or axially overlaps the distal end 692 of the retrograde-delivered guidewire 690. Then a balloon catheter 666, including an elongate shaft 670 and a distal balloon 672, can be advanced over the antegrade-delivered guidewire 698 to a position at or near the guidewire's distal end 691, as illustrated in FIGS. 6E-F. The elongate shaft can be eccentrically coupled to the balloon (FIG. 5A), and the balloon can be formed from an inflatable tube coiled in a helical or spiral manner around a central axis into a series of windings. The structure of the balloon catheter 666, and particularly the balloon 672, allows the catheter to have a smaller outer diameter when it is inserted into a patient's body and maneuvered to the desired position prior to inflation.

In many instances, both the antegrade- and retrograde-delivered guidewires 698, 690 lay in the subintimal space at the occlusion site 606 and are seen as parallel to each other in multiple angiographic views, but they fail to meet in the same plane. To form a connection zone, the balloon 672 on the antegrade guidewire can be inflated to enlarge the antegrade subintimal space 624, as illustrated in FIGS. 6G-H. A distal end 692 of the retrograde-delivered guidewire 690, optionally supported by the specialty catheter 650, can then be manipulated to enter the enlarged antegrade subintimal space 624, thereby completing a true lumen-to-true lumen pathway between the proximal and distal sides of the occlusion 606 and allowing the retrograde guidewire 690 to enter into the proximal true lumen 626.

One problem that can be encountered when seeking to connect the retrograde-delivered guidewire 690 with the enlarged subintimal space 624 is the immediate recoil of such space when the balloon is deflated. Advantageously, the structure of the specialized balloon 672 used according to the present methods forms a passage 668 for receiving the retrograde-delivered guidewire 690 while inflated, as illustrated in FIG. 6I. When the balloon 672 is inflated, the passage 668, which can have a diameter ranging from 2 mm-6 mm and a length ranging from 10 mm-50 mm, for example, is formed and is configured to receive the retrograde guidewire 690. In effect, the balloon 672 performs the functions of a balloon, by creating an enlarged antegrade subintimal space 624, and a stent, by resisting subintimal recoil while providing an open target for retrograde crossing.

During retrograde procedures, retrieving a retrograde-delivered guidewire from a position near the proximal cap 610 of the occlusion 606 can be difficult, time-consuming and frustrating for the treating clinician. Manipulation of guidewire retrieval snares, for example, can be inherently dangerous (e.g., can lead to luminal wall skiving or perforation), unreliable, damaging to the guidewire, and time-consuming. The present methods improve upon existing retrograde capture techniques, specifically guidewire capture techniques. With the distal end 692 of the retrograde-delivered guidewire 690 positioned within the passage 668 of the balloon 672, the balloon can be deflated thereby clamping the guidewire against a wall of the collapsed passage, as shown in FIG. 6J. The balloon catheter 666 and the retrograde-delivered guidewire 690 now act as a combined unit, such that as the balloon 672 is pulled back into the antegrade guide catheter 634, the guidewire 690 is also moved into the antegrade guide catheter 634, as further illustrated in FIG. 6J. This accomplishes the goal of connecting the retrograde-delivered guidewire 690 and the antegrade guide catheter 634. Optionally, the balloon catheter 666 can include one or more radiopaque markers 697, which can help the treating clinician verify that the balloon is properly positioned within the antegrade guide catheter 634.

Once a connection is made between the devices delivered from opposite ends of the occlusion, either through or around the occlusion, one of the guidewires and/or specialty catheters are either extended or exchanged and externalized so that treatment equipment, such as balloon angioplasty equipment and stents, can be passed over the guidewire and used to open the blockage. By way of example, following externalization of the retrograde-delivered guidewire, a balloon angioplasty and stenting treatment procedure can be performed in the antegrade direction using the guidewire as a rail.

If the retrograde-delivered guidewire is not long enough to be externalized or if the guidewire's properties are not as desired by the treating clinician, then the retrograde specialty catheter can be advanced into the antegrade guide catheter over the retrograde guidewire. Once a connection is made between the antegrade guide catheter and the retrograde specialty catheter, the retrograde guidewire used to cross the occlusion can be removed and exchanged for a long wire, which is advanced through the retrograde specialty catheter, the antegrade guide catheter and the guide catheter's hemostatic valve with the objective of converting the revascularization procedure to an antegrade approach.

DEFINITIONS

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document.

The terms "proximal" and "distal," when used to describe portions of an occlusion, refer to a position relative to blood flow direction. "Proximal" refers to an occlusion portion that first encounters blood flow. "Distal" refers to an occlusion portion that subsequently or does not encounter blood flow.

The terms "proximal" and "distal," when used to describe portions of a medical device, refer to a position relative to a treating clinician. "Proximal" and "proximally" refer to a device portion that is closer to the clinician. "Distal" and "distally" refer to a device portion that is distant from the clinician and opposite the proximal direction.

The terms "clinician" or "treating clinician" refer to a doctor, nurse or other care provider and can include support personnel.

The term "patient" refers to mammals and includes both humans and animals.

The term "specialty catheter" refers to a micro-catheter or a support catheter used to provide support to, or exchange of, a guidewire.

The singular forms "a", "an", and "the" include plural referents unless the content clearly dictates otherwise. As used in this specification and the appended claims, the term "or" is generally employed in its sense including "and/or" unless the content clearly dictates otherwise.

All numeric values are assumed to be modified by the term "about," whether or not explicitly indicated. The term "about" refers to a range of numbers that one of skill in the art would consider equivalent to the recited value (e.g., having the same function or result). In many instances, the term "about" can include numbers that are rounded to the nearest significant figure.

The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.).

Closing Notes:

Numerous solutions have been offered in the field of interventional cardiology and radiology to address the treatment of occluded blood vessels in the human body. Some of these vessels may have a CTO, in which the vessel is completely occluded and no longer enables the passage of blood.

Chronic total occlusions are one of the most challenging lesion subsets in interventional cardiology and radiology to treat due to their established occlusive structure, and a quarter of CTOs can only be crossed used a retrograde approach. A limiting step of existing retrograde techniques is making the connection between antegrade- and retrograde-delivered devices advanced across an occlusion and retrieving the retrograde-delivered device from a false subintimal lumen back into the true vessel lumen. The present methods improve upon existing retrograde techniques by providing a treating clinician with novel uses for an inflatable device having a passage, including connecting antegrade and retrograde paths across the occlusion and capturing a distal end of a retrograde-delivered device to move it from the false lumen into the true vessel lumen. This can allow for, among other things, shorter procedure times, reduced radiation exposure for the treating clinician and patient, and less medical waste.

The above Detailed Description includes references to the accompanying drawings, which form a part of the Detailed Description. The Detailed Description should be read with reference to the drawings. The drawings show, by way of illustration, specific embodiments in which the present methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a method can comprise engaging a first guide within a vessel wall adjacent to a distal cap of an occlusion and advancing the first guide, in a retrograde direction, to a subintimal position near a proximal cap of the occlusion. A second guide can be engaged within the proximal cap or the vessel wall adjacent to the proximal cap and advanced, in an antegrade direction, until its distal end is near or axially overlaps a distal end of the first guide. A first vessel lumen, formed by advancement of the first guide, and a second vessel lumen, formed by advancement of the second guide, can be connected by inflating a balloon positioned at or near the distal end of the second guide. The distal end of the first guide can subsequently be received by a passage of the inflated balloon.

In Example 2, the method of Example 1 can optionally further comprise advancing the first guide, in the retrograde direction, toward the distal cap prior to its engagement within the vessel wall.

In Example 3, the method of any one of Examples 1 or 2 can optionally further comprise advancing the second guide, in the antegrade direction, toward the proximal cap of the occlusion prior to its engagement within the proximal cap or the vessel wall adjacent to the proximal cap.

In Example 4, the method of any one of Examples 1-3 can optionally be configured such that engaging the first guide within the vessel wall includes engaging a retrograde-delivered guidewire within the vessel wall, and engaging the second guide within the proximal cap or the vessel wall adjacent to the proximal cap includes engaging an antegrade-delivered guidewire within the proximal cap or the vessel wall adjacent to the proximal cap.

In Example 5, the method of Example 4 can optionally further comprise advancing the balloon to the position at or near the distal end of the second guide along the antegrade-delivered guidewire.

In Example 6, the method of any one of Examples 1-3 can optionally be configured such that engaging the first guide within the vessel wall includes engaging a retrograde-delivered specialty catheter within the vessel wall, and engaging the second guide within the proximal cap or the vessel wall adjacent to the proximal cap includes engaging an antegrade-delivered specialty catheter within the proximal cap or the vessel wall adjacent to the proximal cap.

In Example 7, the method of any one of Examples 1-6 can optionally further comprise deflating the balloon and collapsing the passage, thereby clamping or otherwise capturing the distal end of the first guide against a wall of the collapsed passage.

In Example 8, the method of Example 7 can optionally further comprise guiding the distal end of the first guide into an antegrade guide catheter by pulling the balloon, in the retrograde direction, into the antegrade guide catheter.

In Example 9, the method of Example 8 can optionally further comprise advancing, in the retrograde direction, a specialty catheter over the first guide and into the antegrade guide catheter to complete a pathway between a proximal end of the specialty catheter and a proximal end of the antegrade guide catheter.

In Example 10, the method of Example 9 can optionally further comprise removing the first guide by pulling on its proximal end, in the antegrade direction.

In Example 11, the method of Example 10 can optionally further comprise advancing a third guide having a length longer than a length of the first guide, in the retrograde direction, through the specialty catheter and the antegrade guide catheter and out the proximal end of the antegrade guide catheter.

In Example 12, the method of Example 11 can optionally further comprise performing a revascularization procedure using a treatment device advanced in the antegrade direction along the third guide.

In Example 13, the method of any one of Examples 1-12 can optionally be configured such that inflating the balloon includes inflating a tube coiled in a helical manner around a central axis into a series of windings, with adjacent windings stacked against and bonded to each other.

In Example 14, the method of Example 13 can optionally further comprise advancing the balloon to the position at or near the distal end of the second guide using an elongate shaft eccentrically positioned relative to the helically coiled inflatable tube, prior to the balloon's inflation.

In Example 15, the method of Example 14 can optionally be configured such that inflating the balloon includes providing inflation fluid through a lumen of the elongate shaft.

In Example 16, the method of Example 15 can optionally be configured such that advancing the balloon to the position at or near the distal end of the second guide includes using a guidewire lumen, which is separate from the lumen of the elongate shaft and the passage of the inflated balloon.

In Example 17, the method of any one of Example 13-16 can optionally be configured such that inflating the balloon includes forming the passage.

In Example 18, the method of Example 17 can optionally be configured such that forming the passage includes forming a cavity having a diameter ranging from 2 mm-6 mm and a length ranging from 10 mm-50 mm.

In Example 19, a method of facilitating treatment of a blood vessel can comprise advancing a retrograde-delivered guidewire into subintimal space within a vascular wall and adjacent to a distal cap of an occlusion until its distal end is near a proximal cap of the occlusion. An antegrade-delivered guidewire can be advanced into subintimal space within the vascular wall or within the proximal cap until its distal end is near or overlaps the distal end of the retrograde-delivered guidewire. A first vessel lumen, formed by advancement of the retrograde-delivered guidewire, and a second vessel lumen, formed by advancement of the antegrade-delivered guidewire, can be connected by inflating a balloon positioned at or near the distal end of the antegrade-delivered guidewire. The retrograde-delivered guidewire can then be further advanced into a passage of the inflated balloon, and the balloon can be deflated to collapse the passage. By collapsing the passage, the distal end of the retrograde-delivered guidewire can be captured against a passage wall.

In Example 20, the method of Example 19 can optionally further comprise advancing the retrograde-delivered guidewire through a proximal end of a collateral channel to the distal cap of the occlusion, prior to its advancement into subintimal space.

In Example 21, the method of any one of Examples 19 or 20 can optionally further comprise guiding the distal end of the retrograde-delivered guidewire into an antegrade guide catheter through pulling of the balloon into the antegrade guide catheter.

In Example 22, the method of any one of Examples 19-21 can optionally be configured such that inflating the balloon includes distending a portion of tissue along the innermost surface of the vascular wall.

In Example 23, the method of any one of Examples 19-22 can optionally be configured such that inflating the balloon includes selectively forming a passage between the subintimal space and the vascular lumen.

In Example 24, the method of any one of Examples 19-23 can optionally further comprise performing an interventional procedure over a guidewire disposed partially in the subintimal space.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects. It is to be understood that although dependent claims may be set out in single dependent form, the features of these claims can be combined as if the claims were in multiple dependent form.

The Abstract is provided to allow the reader to quickly ascertain the nature of the technical disclosure. It is submitted with the understanding that it will not be used to interpret or limit the scope or meaning of the claims.

What is claimed is:

1. A method, comprising:
   engaging a first guide within a vessel wall adjacent to a distal cap of an occlusion and advancing the first guide, in a retrograde direction, to a subintimal position near a proximal cap of the occlusion;
   engaging a second guide within the proximal cap or the vessel wall adjacent to the proximal cap and advancing the second guide, in an antegrade direction, until its distal end is near or axially overlaps a distal end of the first guide;
   connecting a first vessel lumen, formed by advancement of the first guide, and a second vessel lumen, formed by advancement of the second guide, including inflating a balloon positioned at or near the distal end of the second guide; and
   receiving the distal end of the first guide within a passage of the inflated balloon.

2. The method of claim 1, further comprising advancing the first guide, in the retrograde direction, toward the distal cap prior to its engagement within the vessel wall.

3. The method of claim 1, further comprising advancing the second guide, in the antegrade direction, toward the proximal cap prior to its engagement within the proximal cap or the vessel wall adjacent to the proximal cap.

4. The method of claim 1, wherein engaging the first guide within the vessel wall includes engaging a retrograde-delivered guidewire within the vessel wall, and engaging the second guide within the proximal cap or the vessel wall adjacent to the proximal cap includes engaging an antegrade-delivered guidewire within the proximal cap or the vessel wall adjacent to the proximal cap.

5. The method of claim 4, further comprising advancing the balloon to the position at or near the distal end of the second guide along the antegrade-delivered guidewire.

6. The method of claim 1, wherein engaging the first guide within the vessel wall includes engaging a retrograde-delivered specialty catheter within the vessel wall, and engaging the second guide within the proximal cap or the vessel wall adjacent to the proximal cap includes engaging an antegrade-delivered specialty catheter within the proximal cap or the vessel wall adjacent to the proximal cap.

7. The method claim 1, further comprising deflating the balloon and collapsing the passage, including clamping a wall of the collapsed passage against the distal end of the first guide.

8. The method of claim 7, further comprising guiding the distal end of the first guide into an antegrade guide catheter by pulling the balloon, in the retrograde direction, into the antegrade guide catheter.

9. The method of claim 8, further comprising advancing, in the retrograde direction, a specialty catheter over the first guide and into the antegrade guide catheter to complete a pathway between a proximal end of the specialty catheter and a proximal end of the antegrade guide catheter.

10. The method of claim 9, further comprising removing the first guide by pulling on its proximal end, in the antegrade direction.

11. The method of claim 10, further comprising advancing a third guide having a length longer than a length of the first guide, in the retrograde direction, through the specialty catheter and the antegrade guide catheter and out the proximal end of the antegrade guide catheter.

12. The method of claim 11, further comprising performing a revascularization procedure using a treatment device advanced in the antegrade direction along the third guide.

13. The method of claim 1, wherein inflating the balloon includes inflating a tube coiled in a helical manner around a central axis into a series of windings, with adjacent windings stacked against and bonded to each other.

14. The method of claim 13, further comprising advancing the balloon to the position at or near the distal end of the second guide using an elongate shaft eccentrically positioned relative to the helically coiled inflatable tube.

15. The method of claim 14, wherein inflating the balloon includes providing inflation fluid through a lumen of the elongate shaft.

16. The method of claim 15, wherein advancing the balloon to the position at or near the distal end of the second guide includes using a guidewire lumen, separate from the lumen of the elongate shaft and the passage of the inflated balloon.

17. The method of claim 1, wherein inflating the balloon includes forming the passage.

18. The method of claim 17, wherein forming the passage includes forming a cavity having a diameter ranging from 2 mm-6 mm and a length ranging from 10 mm-50 mm.

19. A method of facilitating treatment of a blood vessel having a vascular wall, an innermost surface of the vascular wall defining a vascular lumen having an occlusion therein, the vascular wall having an outermost surface further from the vascular lumen, comprising:

advancing a retrograde-delivered guidewire into subintimal space within the vascular wall and adjacent to a distal cap of the occlusion until its distal end is near a proximal cap of the occlusion;

advancing an antegrade-delivered guidewire into subintimal space within the vascular wall or within the proximal cap until its distal end is near or overlaps the distal end of the retrograde-delivered guidewire;

connecting a first vessel lumen, formed by advancement of the retrograde-delivered guidewire, and a second vessel lumen, formed by advancement of the antegrade-delivered guidewire, including inflating a balloon positioned at or near the distal end of the antegrade-delivered guidewire;

further advancing the retrograde-delivered guidewire into a passage of the inflated balloon; and deflating the balloon and collapsing the passage, including capturing the distal end of the retrograde-delivered guidewire using a wall of the collapsed passage.

20. The method of claim 19, further comprising advancing the retrograde-delivered guidewire through a proximal end of a collateral channel to the distal cap prior to its advancement into subintimal space.

21. The method of claim 19, further comprising guiding the distal end of the retrograde-delivered guidewire into an antegrade guide catheter through pulling of the balloon into the antegrade guide catheter.

22. The method of claim 19, wherein inflating the balloon includes distending a portion of tissue along the innermost surface of the vascular wall.

23. The method of claim 19, wherein inflating the balloon includes selectively forming a passage between the subintimal space and the vascular lumen.

24. The method of claim 19, further comprising performing an interventional procedure over a guidewire disposed partially in the subintimal space.

\* \* \* \* \*